(12) United States Patent
Zhou et al.

(10) Patent No.: US 12,403,509 B2
(45) Date of Patent: Sep. 2, 2025

(54) IN-SITU STATE OF FLUID SENSOR

(71) Applicant: Aktiebolaget SKF, Gothenburg (SE)

(72) Inventors: Yu Xin Zhou, Shanghai (CN); Yunfei Pan, Shanghai (CN); Xing Yi, Shanghai (CN); Bo Han, Shanghai (CN); Defeng Lang, Delft (NL)

(73) Assignee: Aktiebolaget SKF, Gothenburg (SE)

( * ) Notice: Subject to any disclaimer, the term of this patent is extended or adjusted under 35 U.S.C. 154(b) by 263 days.

(21) Appl. No.: 17/960,431

(22) Filed: Oct. 5, 2022

(65) Prior Publication Data
US 2023/0128092 A1   Apr. 27, 2023

(30) Foreign Application Priority Data

Oct. 25, 2021   (CN) .......................... 202111239599.0

(51) Int. Cl.
 *G01N 11/16*   (2006.01)
 *B08B 3/02*   (2006.01)

(52) U.S. Cl.
 CPC .............. *B08B 3/024* (2013.01); *G01N 11/16* (2013.01); *B08B 2240/00* (2013.01)

(58) Field of Classification Search
 None
 See application file for complete search history.

(56) References Cited

U.S. PATENT DOCUMENTS

| | | | | |
|---|---|---|---|---|
| 10,293,794 | B2 * | 5/2019 | McAndrew | ............... B60S 1/56 |
| 2018/0178259 | A1 * | 6/2018 | Gillies | ................... H04N 23/51 |
| 2019/0375378 | A1 * | 12/2019 | Nezu | ......................... B08B 5/02 |

FOREIGN PATENT DOCUMENTS

| | | | | |
|---|---|---|---|---|
| CA | 2506165 | A1 | 11/2005 | |
| EP | 3214424 | A1 * | 9/2017 | |
| EP | 3481683 | A1 * | 5/2019 | .............. B08B 3/02 |
| EP | 3686068 | A1 | 7/2020 | |
| EP | 3481683 | B1 | 10/2020 | |
| JP | H09329594 | A | 12/1997 | |
| JP | 2008241289 | A | 10/2008 | |
| WO | WO-2021089241 | A1 * | 5/2021 | .............. B08B 3/02 |

* cited by examiner

*Primary Examiner* — John E Breene
*Assistant Examiner* — Nigel H Plumb
(74) *Attorney, Agent, or Firm* — GARCIA-ZAMOR INTELLECTUAL PROPERTY LAW, LLC; Ruy Garcia-Zamor

(57) ABSTRACT

The invention provides a sensor, which includes a sensing surface; a housing including a recess, the sensing surface is located at the bottom of the recess, and the recess includes at least one side wall and an opening circumferentially surrounding the sensing surface. A compressed fluid nozzle is provided in the at least one side wall to nozzle compressed fluid from the compressed fluid nozzle to force the substance on the sensing surface to leave from the opening. This design makes it possible to refresh in situ with good efficiency without involving additional mechanical parts, thus reducing the risk of sensing surface damage, such as scratch wear, in the presence of wear particles.

10 Claims, 1 Drawing Sheet

IN-SITU STATE OF FLUID SENSOR

CROSS-REFERENCE TO RELATED APPLICATIONS

This application claims priority to Chinese Patent Application no. 202111239599.0, filed Oct. 25, 2021, the contents of which is fully incorporated herein by reference.

TECHNICAL FIELD

The invention relates to a sensor, and in particular relates to a sensor which can refresh the material on the sensing surface.

BACKGROUND

Currently, sensors are needed to monitor the state of fluid in many occasions. When monitoring the state of viscoelastic substances/semi-fluid and semi-solid substances (e.g. grease, gel, paste, emulsion, etc.), it is essential that the sensor can successfully capture fresh samples inside the fluid system. Compared with conventional fluid, this kind of material lacks flowability due to its viscoelasticity, and it requires a specific driving force such as shear force or pressure etc., to refresh the sensing surface or remove the old sample from the sensing surface.

According to the current technology, the sensor for this kind of fluid is set at a specific position in a system involving use of the fluid, such as in the grease flow path in the bearing, where it is expected that the sample on the sensing surface can be refreshed by the inherent grease flow field in the system.

However, due to the yield and adhesive properties of viscoelastic materials, this self-flow-refreshing is not effective enough, and it is very difficult to clean when the sensing surface is covered by the accumulation of this material, which hinders the refreshing of new samples and data acquisition. One sensing surface cleaning technology is to use a mechanical rotary scraper (made of PTFE or silicone rubber, for example) to clean the sensing surface, but this requires mechanical driving parts. Once there are hard particle pollutants on the sensing surface, it will increase the design complexity and the risk of mechanical damage, such as abrasion or scratch.

SUMMARY

In view of this, the present invention provides a sensor comprising: a sensing surface; a housing, including a recess, the sensing surface being disposed at the bottom of the recess, and the recess including at least one side wall and an opening surrounding the sensing surface in the circumferential direction; wherein a compressed fluid nozzle is provided in the at least one side wall, to eject a compressed fluid from the compressed fluid nozzle, to force a substance on the sensing surface to leave from the opening.

The forced refreshing mechanism for the sensing surface of the present invention uses compressed fluid to blow away the substance on the sensing surface. Through the existing flow in the system, the new sample to be sensed can reach the sensing surface again and gather at the top of the sensing surface, reaching the side wall on the sensor housing, to be blocked and gathered.

The sensor based on the invention can realize the feeding and refreshing of fluid substances on the sensing surface, so as to better capture the updated substance sample signal. This will realize the sample renewal on the sensing surface, and can effectively collect the in-situ material conditions inside the system.

This design makes it possible to refresh in situ with good efficiency without involving additional mechanical parts, thus reducing the risk of sensing surface damage in the presence of wear particles (such as scratching).

BRIEF DESCRIPTION OF THE DRAWINGS

At least one of the embodiments of the present invention is accurately represented by this application's drawings which are relied on to illustrate such embodiment(s) to scale and the drawings are relied on to illustrate the relative size, proportions, and positioning of the individual components of the present invention accurately relative to each other and relative to the overall embodiment(s). Those of ordinary skill in the art will appreciate from this disclosure that the present invention is not limited to the scaled drawings and that the illustrated proportions, scale, and relative positioning can be varied without departing from the scope of the present invention as set forth in the broadest descriptions set forth in any portion of the originally filed specification and/or drawings. Through the following drawings, those skilled in the art will have a better understanding of this disclosure, and the advantages of this disclosure can be more clearly reflected.

DETAILED EMBODIMENTS OF THE INVENTION

Figure 1:
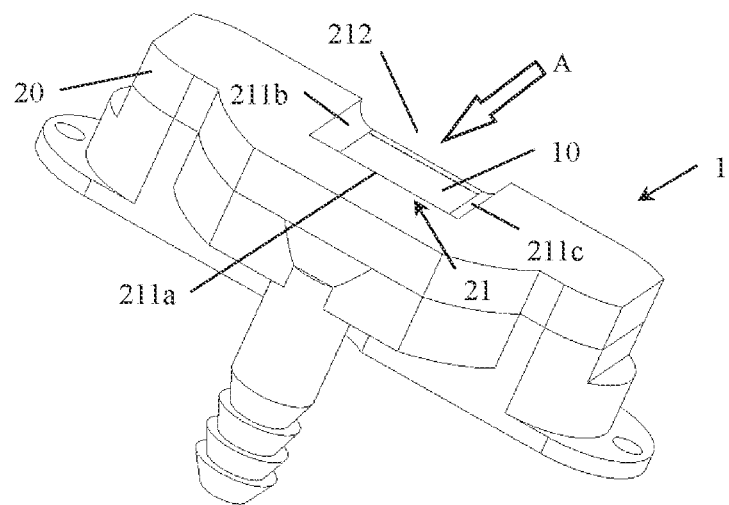
FIGS. 1 and 2 are schematic diagrams of a sensor according to an embodiment of the present invention.
Figure 2:
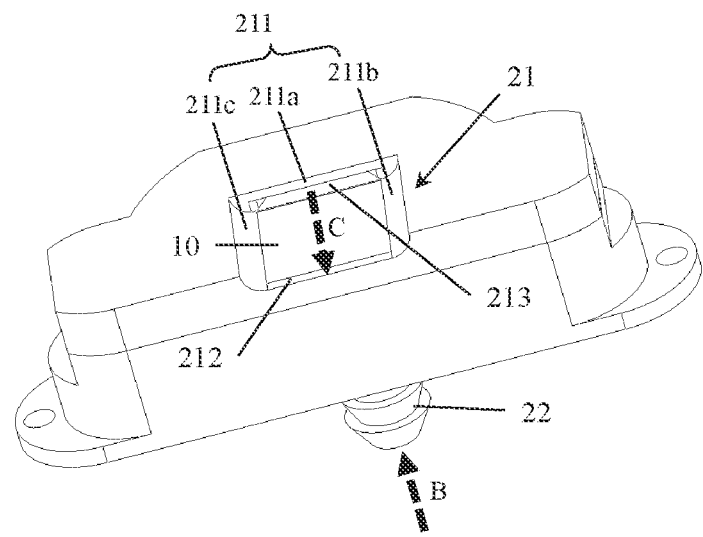

Those of ordinary skill in the art will appreciate from this disclosure that when a range is provided such as (for example) an angle/distance/number/weight/volume/spacing being between one (1 of the appropriate unit) and ten (10 of the appropriate units) that specific support is provided by the specification to identify any number within the range as being disclosed for use with a preferred embodiment. For example, the recitation of a percentage of copper between one percent (1%) and twenty percent (20%) provides specific support for a preferred embodiment having two point three percent (2.3%) copper even if not separately listed herein and thus provides support for claiming a preferred embodiment having two point three percent (2.3%) copper. By way of an additional example, a recitation in the claims and/or in portions of an element moving along an arcuate path by at least twenty) (20° degrees, provides specific literal support for any angle greater than twenty) (20° degrees, such as twenty-three) (23° degrees, thirty) (30° degrees, thirty-three-point five) (33.5° degrees, forty-five) (45° degrees, fifty-two) (52° degrees, or the like and thus provides support for claiming a preferred embodiment with the element moving along the arcuate path thirty-three-point five) (33.5° degrees. Referring to FIGS. 1 and 2, according to an embodiment of the present invention, a sensor 1 is provided, which comprises: a sensing surface 10 and a housing 20, the housing including a recess 21, the sensing surface 10 being disposed at the bottom of the recess 21 (or to say, being part of the bottom of the recess 21), and the recess 21 including a sidewall 211 and an opening 212 surrounding the sensing surface 10 in the circumferential direction (see FIG. 2). is provided with a compressed fluid nozzle 213 is provided in one of the side walls 211 (the side wall 211a shown in FIG.

2), so as to eject the compressed fluid from the compressed fluid nozzle 213, to force the substance on the sensing surface to leave from the opening.

As mentioned above, the substance on the sensing surface may be viscoelastic/semi-solid and semi-fluid substance such as grease and gel, which forms shear flow or pressure flow, and the flow direction is shown by arrow A in FIG. 1, for example. This shear flow or pressure flow, for example, is approximately parallel to the sensing surface.

Furthermore, there wide choices for the compressed fluid according to different substances targeted by the sensor, such as compressed air, compressed nitrogen, high-pressure liquid, etc., as long as it is suitable for removing the substances on the sensing surface and basically does not affect the substance and the working performance of the system. According to the embodiment shown in FIGS. 1 and 2, the compressed fluid is preferably implemented as compressed air.

The sensing surface is preferably a flat surface and can have various geometric shapes. Therefore, the compressed fluid nozzle can be arranged at the position opposite to the opening according to the geometry of the sensing surface. With this arrangement, the compressed fluid can make the substance on the sensing surface leave the opening smoothly.

For example, according to the preferred embodiment shown in FIGS. 1 and 2, the sensing surface 10 is formed as a rectangular sensing surface, the recess 21 includes three side walls 211a, 211b and 211c and one opening 212 surrounding the rectangular sensing surface in the circumferential direction, and the compressed fluid nozzle 213 is disposed at the side wall 211a opposite to the opening 212, for example. FIG. 2 shows the flow direction of the compressed fluid, which enters from the compressed fluid inlet 22 located at the bottom of the housing 20 (for example, connected, as shown by arrow B, to the compressed fluid source via a hose (not shown)), and is ejected from the compressed fluid nozzle 213 (as shown by the dotted arrow C), so as to blow the substance on the sensing surface 10 away from the opening 212.

For example, in an embodiment not shown, the sensing surface may be formed as a circular sensing surface, and the recess may include one arc-shaped side wall and one arc-shaped opening surrounding the circular sensing surface in the circumferential direction, and the compressed fluid nozzle is disposed in the one arc-shaped side wall at a position opposite to the one arc-shaped opening. For example, the one arc-shaped side wall can take the form of a superior arc, an inferior arc or a semi-circular arc around the circular sensing surface in the circumferential direction, and the missing arc-shaped part correspondingly forms the one arc-shaped opening. In the direction perpendicular to the sensing surface, the arc-shaped sidewall and the arc-shaped notch, for example, form a roughly C-shaped shape. Furthermore, the compressed fluid nozzle can be formed at a certain position of the arc-shaped side wall, as long as it ejects the compressed fluid toward the opening to blow off the substance on the sensing surface.

Figure 3A:
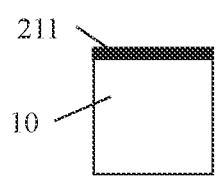
FIGS. 3A and 3B show the arrangement of sensing surfaces and related side walls according to different embodiments of the present invention.
Figure 3B:
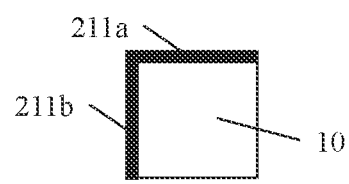

Although the rectangular sensing surface is adopted in the embodiment of FIGS. 1 and 2 and the recess is provided with three side walls, it is conceivable to provide one side wall or two side walls on the sensing surface. As shown in the top view of FIG. 3A, in this embodiment, only one side wall 211 (as shown by the black solid part in FIG. 3A) is formed along one side of the sensing surface 10, while the other three sides have no side walls, forming an open part used as the opening. Accordingly, a compressed fluid nozzle (not shown) can be provided in this one side wall 211. As shown in the top view of FIG. 3B, in this embodiment, two side walls 211a and 211b (as shown by the black solid part in FIG. 3B) are provided along both sides of the sensing surface 10. And accordingly, a compressed fluid nozzle (not shown) can be provided in any of the two side walls 211a and 211b. Therefore, according to the present invention, there may be at least one side wall circumferentially surrounding the sensing surface.

Furthermore, according to other embodiments not shown, the sensing surface may be formed as a polygonal sensing surface, the recess includes at least one side wall and one opening surrounding the polygonal sensing surface in the circumferential direction, and the compressed fluid nozzle is disposed at the side wall opposite to the one opening.

As mentioned above, the substance on the sensing surface comprises, for example, a viscoelastic substance which flows through the sensing surface in a manner of shear flow or pressure flow, so that the compressed fluid nozzle is disposed to eject compressed fluid in a direction opposite to (or to say, contrary to) the direction of the shear flow or the pressure flow. For example, in the embodiment shown in FIGS. 1 and 2, the fluid ejected from the compressed fluid nozzle 213 (dotted arrow C in FIG. 2) is opposite to the direction of shear flow or pressure flow (arrow A in FIG. 1). By such a preferred design, the substance just removed by the compressed fluid will not be pushed back to the sensing surface 10 immediately, so as to facilitate the sufficient refreshing of the sensed sample.

Of course, according to the specific situation of the sensor and the structure it is applied, it is also possible to set the compressed fluid nozzle to eject the compressed fluid in a direction perpendicular or inclined to the direction of the shear flow or pressure flow, so that the sensor and its surface substance cleaning/refreshing mechanism can be designed more flexibly to meet different needs.

According to the embodiment described in FIGS. 1 and 2, the compressed fluid nozzle 213 may have a narrow and long rectangular shape in a cross section perpendicular to the compressed fluid ejection direction (the direction indicated by the dotted arrow C in FIG. 2), for example. Of course, it is also conceivable to adopt other compressed fluid nozzles with cross-sectional shapes, and the number of the compressed fluid nozzles can be one or more.

According to different embodiments, the compressed fluid nozzle can eject compressed fluid in a direction parallel or inclined to the sensing surface. In the embodiment shown in FIGS. 1 and 2, the compressed fluid nozzle 213 ejects compressed fluid in a direction generally parallel to the sensing surface 10, but according to different situations, it is also possible to eject compressed fluid obliquely toward the sensing surface (for example, aligning with the sensing surface or offset from the sensing surface) by setting the internal flow guiding structure of the compressed fluid nozzle.

In addition, since the sensor according to the present invention can be applied to a variety of different viscous and viscoelastic fluids, the compressed fluid can be ejected at a prescribed frequency for a certain time according to the characteristics of the substance on the sensing surface and the status of the system flow field (for example, once an hour for grease and lasting for 60 seconds or more, etc.), so that the substance on the sensing surface can be more sufficiently removed, to refresh the sample to be sensed. Moreover, the pressure of the compressed fluid can also be appropriately selected according to different applications, as long as it can sufficiently remove the substances on the sensing surface without affecting the refreshing of the sample to be sensed.

Furthermore, according to a further preferred embodiment, the sensing surface can be surface treated to have a property of being repel the substance on the sensing surface, such as setting an oleophobic coating for grease or lubricant. This can help to remove the accumulated substances on the sensing surface smoothly.

The exemplary implementation of the scheme proposed in this disclosure has been described in detail above with reference to the preferable embodiments. However, it can be understood by those skilled in the art that without departing from the concept of this disclosure, various changes and modifications can be made to the above specific embodiments, and various technical features and structures proposed in this disclosure can be combined in various ways without exceeding the scope of protection of this disclosure, which is determined by the appended claims.

The invention claimed is:

1. A sensor, comprising:
   a flat rectangular sensing surface;
   a housing, including a recess, the sensing surface being disposed at the bottom of the recess, and the recess including at least one side wall and an opening surrounding the sensing surface in the circumferential direction;
   wherein a compressed fluid nozzle is provided in the at least one side wall, to eject a compressed fluid from the compressed fluid nozzle, to force a substance on the sensing surface to leave from the opening; and
   wherein the sensing surface and the opening of the compressed fluid nozzle are the same width.

2. The sensor according to claim 1, wherein the compressed fluid nozzle is disposed at a position opposite to the opening according to the geometry of the sensing surface.

3. The sensor according to claim 2, wherein the sensing surface is formed as a polygonal sensing surface, the recess includes at least one side wall and one opening surrounding the polygonal sensing surface in the circumferential direction, and the compressed fluid nozzle is disposed at the side wall opposite to the one opening.

4. The sensor according to claim 2, wherein the sensing surface is formed as a circular sensing surface, the recess includes one arc-shaped side wall and one arc-shaped opening surrounding the circular sensing surface in the circumferential direction, and the compressed fluid nozzle is disposed in the one arc-shaped side wall at a position opposite to the one arc-shaped opening.

5. The sensor according to claim 1, wherein the substance on the sensing surface comprises a viscoelastic substance which flows through the sensing surface in a manner of shear flow or pressure flow, and the compressed fluid nozzle is disposed to eject compressed fluid in a direction opposite to the direction of the shear flow or the pressure flow.

6. The sensor according to claim 1, wherein the substance on the sensing surface comprises a viscoelastic substance which flows through the sensing surface in a manner of shear flow or pressure flow, and the compressed fluid nozzle is disposed to eject compressed fluid in a direction perpendicular or inclined to the direction of the shear flow or the pressure flow.

7. The sensor according to claim 1, wherein the compressed fluid nozzle ejects compressed fluid in a direction parallel or inclined to the sensing surface.

8. The sensor according to claim 1, wherein the compressed fluid comprises any one of compressed air, compressed nitrogen and high-pressure liquid.

9. The sensor according to claim 1, wherein the compressed fluid is sprayed at a prescribed frequency for a certain time according to the properties of substances on the surface of the sensor.

10. The sensor according to claim 1, wherein the sensing surface is surface-treated to have a property of being alienated from the substance on the sensing surface.

* * * * *